United States Patent
Kortz et al.

(10) Patent No.: US 7,858,814 B2
(45) Date of Patent: Dec. 28, 2010

(54) RU-CONTAINING POLYOXOTUNGSTATES AND PROCESS FOR THEIR PREPARATION

(75) Inventors: Ulrich Kortz, Bremen (DE); Elena Vladimirovna Chubarova, Stockholm (SE); Nadeen Hassan Nsouli, Bremen (DE)

(73) Assignee: ExxonMobil Chemical Patents Inc., Houston, TX (US)

( * ) Notice: Subject to any disclaimer, the term of this patent is extended or adjusted under 35 U.S.C. 154(b) by 383 days.

(21) Appl. No.: 12/143,628

(22) Filed: Jun. 20, 2008

(65) Prior Publication Data
US 2009/0318723 A1    Dec. 24, 2009

(51) Int. Cl.
- C07F 19/00 (2006.01)
- B01J 23/00 (2006.01)
- C07C 27/10 (2006.01)

(52) U.S. Cl. .......... 556/28; 556/7; 556/9; 502/207; 502/326; 568/956

(58) Field of Classification Search .......... 556/7, 556/9, 28; 568/956; 502/207, 326
See application file for complete search history.

(56) References Cited

U.S. PATENT DOCUMENTS
| | | |
|---|---|---|
| 5,091,354 A | 2/1992 | Ellis, Jr. et al. |
| 5,990,348 A | 11/1999 | Lyons et al. |

FOREIGN PATENT DOCUMENTS
| | | |
|---|---|---|
| JP | 11199594 | 7/1999 |
| WO | WO 03/028881 | 4/2003 |
| WO | WO 2007/139616 | 12/2007 |
| WO | WO 2008/128638 | 10/2008 |

OTHER PUBLICATIONS

Naruke et al., A Novel-Type Mixed-Ligand Polyoxotungstolanthanoate, $[Ln(BW_{11}O_{39})(W_5O_{18})]12-$ (Ln =$Ce^{3+}$ and $Eu^{3+}$), Bulletin Chemical Society of Japan, 2000, vol. 73, No. 2, pp. 375-382.

Bi et al., "A novel isopolytungstate functionalized by ruthenium: $[HW_9O_{33}Ru^{II}{}_2(dmso)_6]^{7-}$," Chem. Commun. 2004, 1420-1421.

(Continued)

*Primary Examiner*—Porfirio Nazario Gonzalez
(74) *Attorney, Agent, or Firm*—Catherine L. Bell

(57) ABSTRACT

The invention relates to polyoxometalates represented by the formula $(A_n)^{m+}$ $[Ru_2L_2(XW_{11}O_{39})_2WO_2]^{m-}$ or solvates thereof, wherein A is a cation, n is the number of the cations, m is the charge of the polyanion, L is a ligand bound to ruthenium and is independently selected from group consisting of water, unsubstituted or substituted arenes, unsubstituted or substituted heteroarenes, unsaturated hydrocarbons, ethers, unsubstituted or substituted allyl, unsubstituted or substituted alkanes, nitriles, carboxylates, peroxides, peracids, phosphines, phosphanes, CO, $OH^-$, peroxo, carbonate, $NO_3^-$, $NO_2^-$, $NO^-$, $NH_3$, amines, $F^-$, $Cl^-$, $Br^-$, $I^-$, $SCN^-$, $NCS^-$, $NCO^-$ and mixtures thereof and X is a heteroatom selected from Si, Ge, B and mixtures thereof, a process for their preparation and their use for the catalytic oxidation of organic molecules.

25 Claims, 1 Drawing Sheet

OTHER PUBLICATIONS

Bi et al., "The Ru(II)-supported heptatungstates [HXW$_7$O$_{28}$Ru(dmso)$_3$]$^{6-}$ (X=P, As)," Chem. Commun. 2005, 3962-3964.

Bi et al., "The ruthenium(II)-supported heteropolytungstates [Ru(dmso)$_3$(H$_2$O)-XW$_{11}$O$_{39}$]$^{6-}$ (X=Ge, Si)," J. Chem. Soc., Dalton Trans. 2004, 3184-3190.

Laurencin et al., "A new organometallic heterppolytungstate related to [Sb$_2$W$_{22}$O$_{74}$(OH)$_2$]$^{12-}$: Synthesis and structural characterization of the bis-{Ru(p-cymene)}$^{2+}$-containing anion [Sb$_2$W$_{22}$O$_{70}${Ru(p-cymene)}$_2$]$^{10-}$," Chemical Communications, vol. 44, 2005, 5524-5526.

Loose et al., "Heteropolymetallate Clusters of the Subvalent Main Group Elements Bi$^{III}$ and S$^{III}$," Inorg. Chem., vol. 38, 1999, 2688-2694.

Nomiya et al., "Synthesis and characterization of a monoruthenium(III)-substituted Dawson polyoxotungstate derived by Br$_2$ oxidation of the 1 : 2 complex of ruthenium(II) and [α$_2$-P$_2$W$_{17}$O$_{61}$]$^{10-}$. The reactivity of cis-[RuCl$_2$(DMSO)$_4$] as a ruthenium source," J. Chem. Soc. Dalton Trans. 2001, 1506-1512.

Artero et al., Synthesis, Characterization, and Photochemical Behavior of {Ru(arene)}$^{2+}$ Derivatives of α-[PW$_{11}$O$_{39}$]$^{7-}$: An Organometallic Way to Ruthenium-Substituted Heteropolytungstates, Inorganic Chemistry, 2005, vol. 44, No. 8, pp. 2826-2835.

Artero et al., Synthesis and Characterization of the First Carbene Derivative of a Polyoxometalate, J. Am. Chem. Soc., 2003, vol. 125, No. 37, pp. 11156-11157.

Bi et al., Dilacunary Decatungstates Functionalized by Organometallic Ruthenium(II), [{Ru(C$_6$H$_6$)(H$_2$O)} {Ru(C$_6$H$_6$)} (γ-XW$_{10}$O$_{36}$)]$^{4-}$ (X=Si, Ge), Inorganic Chemistry, 2006, vol. 45, No. 21, pp. 8575-8583.

Bi et al., Trilacunary Heteropolytungstates Functionalized by Organometallic Ruthenium (II), [(RuC$_6$H$_6$)$_2$XW$_9$O$_{34}$]$^{6-}$ (X=Si, Ge), Inorganic Chemistry, 2005, vol. 44, No. 21, pp. 7485-7493.

Bösing et al., New Strategies for the Generation of Large Heteropolymetalate Clusters: The β- B-SbW$_9$ Fragment as a Multifunctional Unit, Chem. Eur. J., 1997, vol. 3, No. 8, pp. 1232-1237.

Cavani, Heteropolycompound-based catalysts: A blend of acid and oxidizing properties, Catalysis Today, 1998, vol. 41, pp. 73-86.

Cavani et al., Combined effects of Sb-doping and of preparation via lacunary precursor for P/Mo-based, Keggin-type polyoxometalates, catalysts for the selective oxidation of isobutene to methacrylic acid, Topics in Catalysis, 2003, vol. 23, Nos. 1-4, pp. 119-124.

Fay et al., Synthesis and electrochemical of characterization [Ru(bpy)$_3$]$_3$[P$_2$W$_{18}$O$_{62}$], Journal of Electroanalytical Chemistry, 2003, vol. 556, pp. 63-74.

Han et al., Synthesis and crystal structure of a novel compound constructed from tris-(2, 2'-bipy)ruthenium(II) and decatungstate, Inorganic Chemistry Communications, 2001, vol. 4, pp. 427-429.

Kamata et al., Efficient Epoxidation of Olefins with ≥ 99% Selectivity and Use of Hydrogen Peroxide, Science, 2003, vol. 300, pp. 964-966.

Kato et al., Water-soluble organometallic ruthenium(II) complexes supported on Dawson-type polyoxotungstates as precatalysts: Selective oxidation of alcohols with 1 atm molecular oxygen, Catalysis Communications, 2006, vol. 7, pp. 413-416.

Lahootun et al., Synthesis and Characterization of the Keggin-Type Ruthenium-Nitrido Derizative [PW$_{11}$O$_{39}${RuN}]$^{4-}$ and Evidence of its Electrophilic Reactivity, J. Am. Chem. Soc., 2007, vol. 129, No. 22, pp. 7127-7135.

Limanski et al., Syntheses and X-ray characterisation of novel tellurium-substituted lacunary polyoxotungstates containing V$^{IV}$, Co$^{II}$, Ni$^{II}$ and Zn$^{II}$ as heteroatoms, Journal of Molecular Structure, 2003, vol. 656, pp. 17-25.

Mal et al., Organoruthenium derivative of the cyclic [H$_7$P$_8$W$_{48}$O$_{184}$]$^{33-}$ anion: [{K(H$_2$O)}$_3${Ru(p-cymene)(H$_2$O)}$_4$P$_8$W$_{49}$O$_{186}$(H$_2$O$_2$)$_2$]$^{27-}$, Dalton Trans., 2007, pp. 2627-2630.

Misono, Unique acid catalysis of heteropoly compounds (heteropolyoxometalates) in the solid state, Chem. Commun., 2001, pp. 1141-1152.

Misono et al., Recent Progress in Catalytic Technology in Japan, Applied Catalysis, 1990, vol. 64, pp. 1-30.

Neumann, Polyoxometalate Complexes in Organic Oxidation Chemistry, Progress in Inorganic Chemistry, 1998, vol. 47, pp. 317-370.

Neumann et al., Molecular Oxygen Activation by a Ruthenium-Substituted "Sandwich" Type Polyoxometalate, J. Am. Chem. Soc., 1998, vol. 120, No. 46, pp. 11969-11976.

Neumann et al., Hydroxylation of Alkanes with Molecular Oxygen Catalyzed by a New Ruthenium-Substituted Polyoxometalate, [WZnRu$_2^{III}$(OH)(H$_2$O)(ZnW$_9$O$_{34}$)$_2$]$^{11-}$, Angew. Chem. Int. Ed. Engl., 1995, vol. 34, No. 15, pp. 1587-1589.

Neumann et al., A ruthenium-substituted poloxometalate as an inorganic dioxygenase for activation of molecular oxygen, Nature, 1997, vol. 388, pp. 353-355.

Neumann et al., Noble Metal (Ru$^{III}$, Pd$^{III}$, Pt$^{II}$) Substituted "Sandwich" Type Polyoxometalates: Preparation, Characterization, and Catalytic Activity in Oxidations of Alkanes and Alkenes by Peroxides, Inorg. Chem., 1995, vol. 34, No. 23, pp. 5753-5760.

Nomiya et al., Organometallic Complexes Supported on a Metal-Oxide Cluster. pH-Dependent Interconversion between the Monomeric and Dimeric Species of the Polyoxoanion-Supported [(arene)Ru]$^{2+}$ Complex, Bull. Chem. Soc. Jpn., 2007, vol. 80, No. 4, pp. 724-731.

Nsouli et al., Synthesis and Structure of Dilacunary Decatungstogermanate, [γ-GeW$_{10}$O$_{36}$]$^{8-}$, Inorganic Chemistry, 2006, vol. 45, No. 10, pp. 3858-3860.

Rong et al., Lacunary Polyoxometalate Anions Are π-Acceptor Ligands. Characterization of Some Tungstoruthenate(II,III,IV,V) Heteropolyanions and Their Atom-Transfer Reactivity, J. Am. Chem. Soc., 1992, vol. 114, No. 8, pp. 2932-2938.

Sadakane et al., Synthesis and electrochemical behavior of [SiW$_{11}$O$_{39}$Ru$^{III}$(H$_2$O)]$^{5-}$ and its oxo-bridged dimeric complex [SiW$_{11}$O$_{39}$Ru$^{IV}$ORu$^{III}$SiW$_{11}$O$_{39}$]$^{11-}$, Dalton Trans., 2003, pp. 659-664.

Sadakane et al., Structural characterization of mono-ruthenium substituted Keggin-type silicotungstates, Dalton Trans., 2006, pp. 4271-4276.

Sadakane et al., Dimerization of mono-ruthenium substituted α-Keggin-type tungstosilicate [α-SiW$_{11}$O$_{39}$Ru$^{III}$(H$_2$O)]$^{5-}$ to μ-oxo-bridged dimer in aqueous solution: synthesis, structure, and redox studies, Dalton Trans., 2007, pp. 2833-2838.

Sakai et al., Synthesis and Characterization of Two Novel, Mono-Lacunary Dawson Polyoxometalate-Based, Water-Soluble Organometallic Ruthenium (II) Complexes: Molecular Structure of [{(C$_6$H$_6$)Ru(H$_2$O)}(α$_2$-P$_2$W$_{17}$O$_{61}$)]$^{8-}$, Eur. J. Inorg. Chem., 2006, pp. 163-171.

Tézé et al., Syntheses and Structures of the Tungstoborate Anions, Inorg. Chem., 1997, vol. 36, No. 4, pp. 505-509.

Tézé et al., Relationship Between Structures and Properties of Undecatugstosilicate Isomers and of Some Derived Compounds, J. Inorg. Nucl. Chem., 1977, vol. 39, pp. 2151-2154.

Tézé et al., Formation Et Isomerisation Des Undeca Et Dodeca Tungstosilicates Et Germanates Isomeres, J. Inorg. Nucl. Chem., 1997, vol. 39, pp. 999-1002 (w/English Abstract).

Hervé et al., Tetracontatungstotetraarsenate(III) and Its Colbalt (II) Complex, Early Transition Metal Polyoxoanions, Inorganic Syntheses, 1990, vol. 27, pp. 118-120.

Tézé et al., α-, β-, and γ-Dodecatungstosilicic Acids: Isomers and Related Lacunary Compounds, Inorganic Syntheses, 1990, vol. 27, pp. 85-96.

Xu et al., Studies on the Synthesis and Characterization of Sandwich Type Polyoxometalate (Bu$_4$N)$_7$H$_3$[Ru$_2$O(H$_2$O)$_2$(γ-SiW$_{10}$O$_{36}$)$_2$], Chemical Journal of Chinese Universities, 2001, vol. 22, No. 4, pp. 520-523 (w/English Abstract).

Xu et al., Studies on Synthesis and Characterization of Noble-metal (Ru)-Substituted Polyoxometalates, Journal of Fudan University (Natural Science), 2001, vol. 40, No. 4, pp. 424-428 (w/English Abstract).

Yamaguchi et al., Heterogeneously catalyzed liquid-phase oxidation of alkanes and alcohols with molecular oxygen, New J. Chem., 2002, vol. 26, pp. 972-974.

Yin et al., Is It True Dioxygenase or Classic Autoxidation Catalysis? Re-Investigation of a Claimed Dioxygenase Catalyst Based on a Rue-Incorporated, Polyoxometalate Precatalyst, Inorganic Chemistry, 2005, vol. 44, No. 12, pp. 4175-4188.

US 7,858,814 B2

RU-CONTAINING POLYOXOTUNGSTATES AND PROCESS FOR THEIR PREPARATION

STATEMENT OF RELATED CASES

This application is related to U.S. Ser. No. 11/443,683, filed May 31, 2006; U.S. Ser. No. 11/445,073, filed May 31, 2006; Ser. No. 11/445,095, filed May 31, 2006; U.S. Ser. No. 11/655,593, filed Jan. 19, 2007; U.S. Ser. No. 11/728,142, filed Mar. 23, 2007; and U.S. Ser. No. 12/037,647, filed Feb. 26, 2008.

FIELD OF THE INVENTION

This invention relates to new polyoxometalates (POMs) containing ruthenium addenda atoms, a process for their preparation and their use for the catalytic oxidation of organic molecules.

BACKGROUND OF THE INVENTION

POMs are a unique class of inorganic metal-oxygen clusters. They consist of a polyhedral cage structure or framework bearing a negative charge which is balanced by cations that are usually external to the cage, and may also contain centrally located heteroatom(s) surrounded by the cage framework. Generally, suitable heteroatoms include Group 13-16 elements such as phosphorus, antimony, silicon and boron. The framework of POMs comprises a plurality of metal atoms (addenda), which can be the same or different, bonded to oxygen atoms. Up to now the framework metal is substantially limited to a few elements including transition metals from Group 5 and Group 6 in their high oxidation states, e.g. tungsten (VI), molybdenum (VI), vanadium (V), niobium (V) and tantalum (V).

The first example in the POM family is the so-called Keggin anion $[XM_{12}O_{40}]^{3-}$ with X being a heteroatom selected from a wide variety of elements such as P and M being a Group 5 or Group 6 metal such as Mo or W. These anions consist of an assembly of corner- and edge-shared $MO_6$ octahedra of the metals of Groups 5 or 6 around a central $XO_4$ tetrahedron.

In the past, there have been increasing efforts towards the modification of polyoxoanions with various organic and/or transition metal complex moieties with the aim of generating new catalyst systems as well as functional materials with interesting optical, electronic and magnetic properties. In particular, transition metal-substituted polyoxometalates (TMSPs) have attracted continuously growing attention as they can be rationally modified on the molecular level including size, shape, charge density, acidity, redox states, stability, solubility etc. To date many 3d transition metal containing POMs are known, but only a few POMs containing 4d and 5d metals are known. However, the introduction in a POM of 4d and 5d metals appears to be of fundamental interest. Especially, ruthenium containing POMs are of interest because they are thermally and oxidatively stable and possess highly attractive catalytic properties.

For example, Neumann et al. describe the preparation of ruthenium-substituted "sandwich" type polyoxometalate $[WZnRu_2(OH)(H_2O)(ZnW_9O_{34})_2]^{11-}$ as well as its ability to catalyze the oxidation of alkanes and alkenes using hydrogen peroxide and molecular oxygen as the oxygen donor (see: Angew. Chem. Int. Ed. Engl. 1995, 34, 1587; Inorg. Chem. 1995, 34, 5753; J. Am. Chem. Soc. 1998, 120, 11969 and Nature, 1997, 388, 353-355). Moreover, Pope et al., J. Am. Chem. Soc. 1992, 114, 2932, disclose the synthesis of the cesium salt of $[PW_{11}O_{39}Ru(H_2O)]^{4+}$ and characterize its oxygen atom transfer reactivity. In all these syntheses, $RuCl_3 \cdot nH_2O$ or $[Ru(H_2O)_6](C_7H_7SO_3)_2$ are used as ruthenium sources.

Further, $Ru^{3+}$-substituted silicotungstates such as $[SiW_{11}O_{39}Ru^{III}(H_2O)]^{5-}$, its use as catalyst for the oxidation of various alkanes and alcohols and its dimerization to the μ-oxo-bridged dimer $[\{SiW_{11}O_{39}Ru^{III}\}_2O]^{n-}$ have been described (Mizuno et al., New J. Chem., 2002, 26, 972-974; Sadakane et al., Dalton Trans., 2003, 659-664; Sadakane et al., Dalton Trans., 2006, 4271-4276; Sadakane et al. Dalton Trans., 2007, 2833-2838).

Nomiya et al., J. Chem. Soc., Dalton Trans. 2001, 1506, discuss the difficulty of making pure Ru-containing POMs and the non-reproducibility of some reported Ru-substituted polyanions.

Recently, the dimethyl sulfoxide (dmso) complex cis-Ru $(dmso)_4Cl_2$ has become a popular ruthenium(II) source for the synthesis of Ru-substituted POMs. For example, Kortz et al. disclose the preparation and structural characterization of $[HW_9O_{33}Ru_2(dmso)_6]^{7-}$, $[Ru(dmso)_3(H_2O)XW_{O39}]^{6-}$ (X=Ge, Si) and $[HXW_7O_{28}Ru(dmso)_3]^{6-}$ (X=P, As) (see: Chem. Commun. 2004, 1420; J. Chem. Soc., Dalton Trans. 2004, 3184; and Chem. Commun. 2005, 3962).

However, up to now these $Ru^{II}(dmso)_3$-based anions have not turned out to be very useful for homogeneous or heterogeneous catalytic applications.

In addition, the use of a $Ru^{II}$(arene) containing source for the synthesis of Ru-substituted POMs has recently been described. For example, Proust et al. report on the reaction of $[Ru(arene)Cl_2]_2$ with $K_7[\alpha-PW_{11}O_{39}] \cdot 14H_2O$ to obtain the monomeric species $[\alpha-PW_{11}O_{39}\{Ru(arene)(H_2O)\}]^{5-}$ and the dimeric species $[\{\alpha-PW_{11}O_{39}\{Ru(arene)\}\}_2\{WO_2\}]^{8-}$ (Inorg. Chem. 2005, 44, 2826-2835). The formation of the dimeric complexes is reported to depend on the bulkiness of the arene ligand and their isolation is described to be difficult. Nomiya et al., Bulletin of the Chemical Society of Japan, 2007, 80, 724-731, conclude that the steric repulsion between the two (arene)$Ru^{2+}$ fragments in the dimeric species is not significant, the interconversion between the monomeric and the dimeric species is strongly dependent on the pH of the reaction solution rather than the bulkiness of the arene and the use of an in-situ generated POM precursor has an effect.

Moreover, Kortz et al. report on the reaction of $[Ru(C_6H_6)Cl_2]_2$ with $[\gamma-SiW_{10}O_{36}]^{8-}$ and $[\gamma-GeW_{10}O_{36}]^{8-}$, respectively, to yield $[\{Ru(C_6H_6)(H_2O)\}(\gamma-XW_{10}O_{36})]^{4-}$ (X=Si, Ge) (Inorg. Chem. 2006, 45, 8575-8583). Further, the reaction of $[Ru(p-cymene)Cl_2]_2$ with the cyclic $[H_7P_8W_{48}O_{148}]^{33-}$ anion is described to result in $[\{K(H_2O)\}_3\{Ru(p-cymene)(H_2O)\}_4P_8W_{49}O_{186}(H_2O)_2]^{27-}$ having four {Ru(p-cymene)$(H_2O)$} fragments grafted on the crown-shaped $P_8W_{48}$ precursor (Dalton Trans., 2007, 2627-2630). WO-A-2007/139616 discloses the diruthenium containing POM $[Ru_2(H_2O)_6X_2W_{20}O_{70}]^{m-}$ (X=$Sb^{III}$, $Bi^{III}$, $As^{III}$, $Se^{IV}$ or $Te^{IV}$) which has been found to exist in a Krebs-type structure, i.e. a dimeric POM consisting of two trilacunary Keggin fragments B-β-$[XW_9O_{33}]^{p-}$ that are linked by two $\{WO_2\}^{2+}$ and two $\{Ru(H_2O)_3\}^{q+}$ cations.

However, there is still a need for further Ru-containing POMs showing useful properties in homogeneous or heterogeneous catalytic applications.

Therefore, it is an object of the present invention to provide Ru-containing POMs which are useful as catalysts in homogeneous and heterogeneous oxidation reactions of organic substrates. Furthermore, such Ru-containing POMs should be easily and reproducibly prepared in high yield and purity. Moreover, they should be useful as precursors for preparing mixed metal oxide catalysts.

SUMMARY OF THE INVENTION

These objects are achieved by polyoxometalates represented by the formula:

or solvates thereof, wherein:
A is a cation,
n is the number of the cations,
m is the charge of the polyanion,
L is a ligand bound to ruthenium and is independently selected from the group consisting of water, unsubstituted or substituted arenes, unsubstituted or substituted heteroarenes, unsaturated hydrocarbons, ethers, unsubstituted or substituted allyl, unsubstituted or substituted alkanes, nitriles, carboxylates, peroxides, peracids, phosphines, phosphanes, CO, OH$^-$, peroxo, carbonate, NO$_3^-$, NO$_2^-$, NO$^-$, NH$_3$, amines, F$^-$, Cl$^-$, Br$^-$, I$^-$, SCN$^-$, NCS$^-$, NCO$^-$ and mixtures thereof and
X is a heteroatom selected from Si, Ge, B and mixtures thereof.

DETAILED DESCRIPTION

Figure 1:
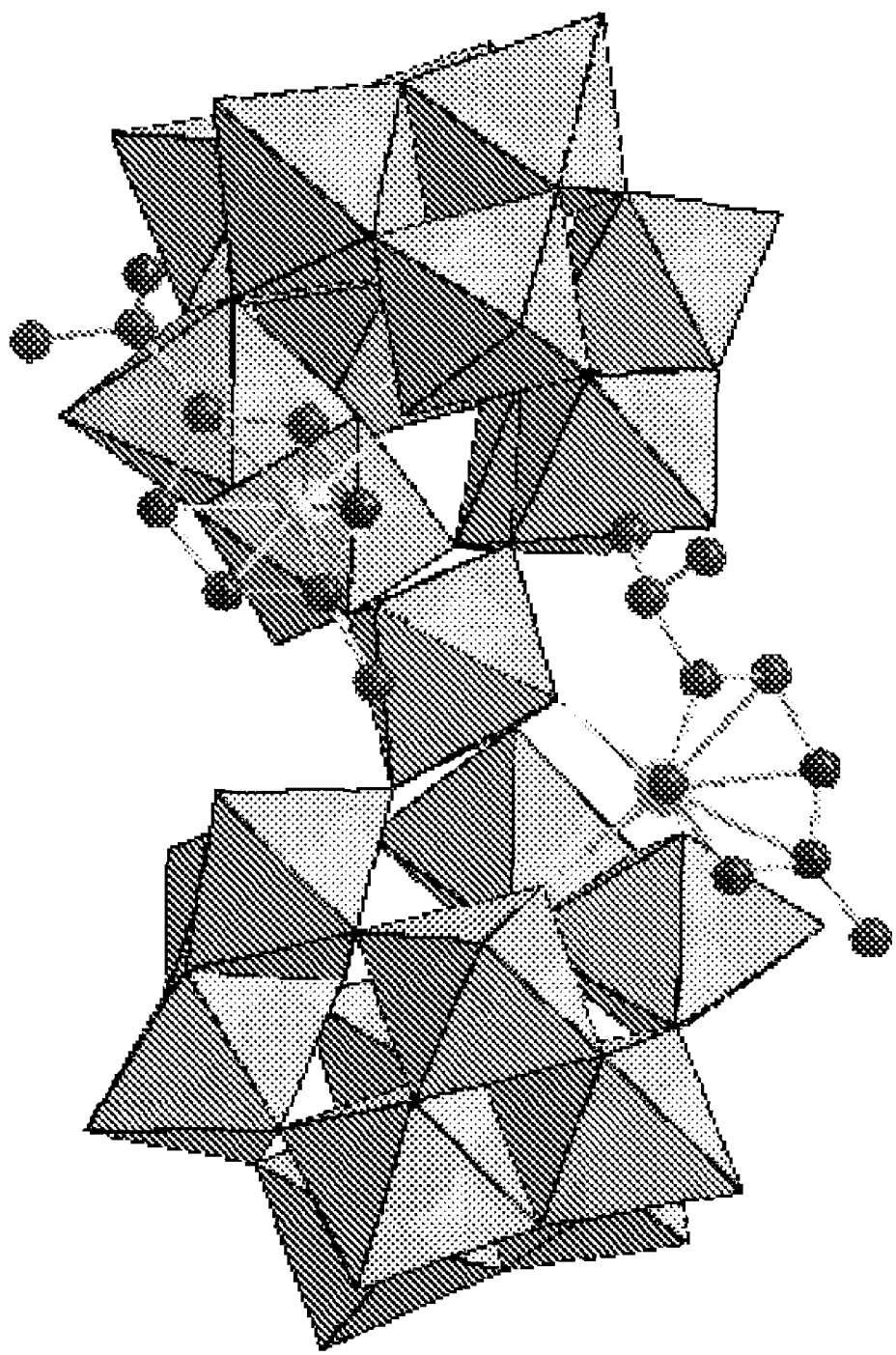
FIG. 1 is an issultration of the structure of [Ru$_2$(p-cymene)$_2$(XW$_{11}$O$_{39}$)$_2$WO$_2$]$^{m-}$.

The polyanion [Ru$_2$L$_2$(XW$_{11}$O$_{39}$)$_2$WO$_2$]$^{m-}$ of the POMs according to the invention has been found to be constituted from the assembly of two [XW$_{11}$O$_{39}${Ru(L)}]$^{q-}$ fragments connected through a cis-dioxo {WO$_2$}$^{2+}$ unit. Compared to the environment of the tungsten atoms of the {XW$_{11}$O$_{39}$} subunits, that of the tungsten atom of the {WO$_2$} group is strongly distorted. The [XW$_{11}$O$_{39}${Ru(L)}]$^{q-}$ fragments each consist of a lacunary {XW$_{11}$O$_{39}$} anion supporting a {Ru(L)} fragment which is bound to two oxygen atoms of the lacuna and to an oxo ligand of the {WO$_2$}$^{2+}$ bridging group.

For example, the structure of [Ru$_2$(p-cymene)$_2$(XW$_{11}$O$_{39}$)$_2$WO$_2$]$^{m-}$ is illustrated in FIG. 1. The balls of this figure represent ruthenium (gray shaded) and carbon of the p-cymene ligand (black). The WO$_6$ units are represented as gray corner- and edge-shared octahedra. The cations A are omitted for clarity.

Preferably, both {XW$_{11}$O$_{39}$} fragments of the present POMs are in the form of the α-isomer. Thus, the POMs according to the invention are preferably represented by the formula:

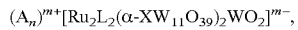

The terms "α" and "β$_2$" used herein refer to the skeletal isomerism of the {XW$_{11}$O$_{39}$} fragments and are used herein in accordance with their usual meaning in the field of polyoxometalates (see e.g.: A. Tézé, G. Hervé, J. Inorg. Nucl. Chem. 1977, 39, 2151-2154)

In comparison to several known Ru-substituted POMs the present POMs are characterized in that the Ru centers are not fully incorporated into the POM framework, but rather grafted on the POM surface. Thus, they are easily accessible for e.g. oxidation agents and organic substrates in redox reactions. This applies all the more as the Ru centers bear substitution labile ligands L. Moreover, the two {Ru(L)} fragments are relatively closely spaced and thus interactions between the two Ru centers are possible. Due to these characteristics a unique catalytic performance in oxidation reactions is achieved.

In a preferred embodiment, the polyoxometalates are represented by the formula:

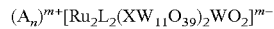

where:

The cation A is preferably hydrogen or a Group 1, 2, 3, 4, 5, 6, 7, 8, 9, 10, 11, 12, 13, 14, 15 and 16 metal or an organic cation. Preferably, A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium such as tetraalkylphosphonium, ammonium, guanidinium, tetraalkylammonium, protonated aliphatic amines, protonated aromatic amines and combinations thereof. More preferably, A is selected from potassium, sodium, cesium, ammonium and combinations thereof.

The number n of cations is dependent on the nature of cation(s) A, namely its/their valence, and the negative charge m of the polyanion which has to be balanced. In any case, the overall charge of all cations A is equal to the charge of the polyanion. In turn, the charge m of the polyanion is dependent on the oxidation state of the Ru centers, the oxidation state of the heteroatoms X and the oxidation state of ligand L. Thus, m depends on the oxidation state of the atoms present in the polyanion, e.g., it follows from the oxidation states of O (−2), X (+3 for B, +4 for Si and Ge), Ru (ranging from +2 to +5, preferably +2, +3, +4 or +5, preferably +2), and L (ranging from 0 to −2, preferably 0, −1 or −2, preferably 0). In some embodiments, m ranges from 10 to 16. In particular, m is 10 or 12. Thus, n can generally range from 2 to 16. In particular, n ranges from 5 to 16 and more particularly is 10 or 12.

Generally, A is acting as counterion of the polyanion and is therefore positioned outside of the POM framework. However, it is also possible that some of the cations A are located within the POM framework. In particular, if hydrogen is present as cation A, said hydrogen cation(s) can be covalently bound to oxygen atoms of the polyanion framework.

In a preferred embodiment, the ligands L bound to ruthenium are independently selected from group consisting of water, unsubstituted or substituted arenes, unsubstituted or substituted heteroarenes, unsaturated hydrocarbons, ethers, unsubstituted or substituted allyl, unsubstituted or substituted alkanes, nitriles, carboxylates, peroxides, peracids, phosphines, phosphanes, CO, OH$^-$, peroxo, carbonate, NO$_3^-$, NO$_2^-$, NO$^-$, NH$_3$, amines, F$^-$, Cl$^-$, Br$^-$, I$^-$, SCN$^-$, NCS$^-$, NCO$^-$ and mixtures thereof.

As used herein, "arene" is an aromatic monocyclic or multicyclic ring system comprising about 6 to about 14 carbon atoms, preferably about 6 to about 10 carbon atoms. Non-limiting examples of suitable arene groups include benzene, toluene, p-cymene, durene, mesitylene and hexamethylbenzene. "Heteroarene" is an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroarenes contain about 5 to about 6 ring atoms. Non-limiting examples of suitable heteroarenes include 2,2'-bipyridine, furane, pyridine, pyrrole, thiophene, pyrimidine, pyrimidazine, pyrazine and the like. An "unsaturated hydrocarbon(s)" is a straight or branched aliphatic hydrocarbon group containing at least one carbon-carbon double bond or at least one carbon-carbon triple bond and having 2 to about 15 carbon atoms. In particular, "unsaturated hydrocarbons" include alkenes and alkynes, such as alpha as well as internal olefins, with up to 5 carbon atoms, and cycloolefins. Preferred alkenes have 2 to about 12 carbon atoms; and more preferably 2 to about 4 carbon atoms. Non-limiting examples of suitable alkenes include ethene, propene and 2-butene. Preferred alkynes have 2 to about 12 carbon atoms and more preferably 2 to about 4 carbon atoms in the chain. Non-limiting examples of suitable alkynes include ethyne, propyne, 2-butyne and 3-methylbutyne. An "alkane" is a straight or branched aliphatic hydrocarbon with 1 to about 20 carbon atoms. Preferred alkanes contain 1 to about 12 carbon atoms. More preferred alkanes contain 1 to about 6 carbon atoms. Non-limiting examples of suitable alkanes include methane, ethane, n-propane, isopropane and t-butane.

In one embodiment, L is selected from the group consisting of water, unsubstituted or substituted arenes and mixtures thereof. Preferably, L is water, benzene, p-cymene, toluene, mesitylene, durene, hexamethylbenzene, 1,3-dimethylimidazolidine-2-ylidene, 2,2'-bipyridine, α- as well as internal olefins with up to 5 carbon atoms such as ethylene, propylene, α-butylene, cis-β-butylene, trans-β-butylene, isobutylene, n-pentylene, and isopentylene, cycloolefins such as cyclooctadiene, tetrahydrofuran, diethyl ether, methyl t-butyl ether or allyl alcohol. More preferably, L is water, benzene, p-cymene, toluene, mesitylene, durene or hexamethylbenzene. Most preferably, L is benzene or p-cymene.

Furthermore, in another embodiment, the heteroatom X is selected from B, Si, Ge and mixtures thereof.

Accordingly, suitable examples of POMs according to the invention are represented by the formula:

$(A_n)^{m+}[Ru_2L_2(SiW_{11}O_{39})_2WO_2]^{m-}$ e.g.

$(A_n)^{10+}[Ru_2(H_2O)_2(SiW_{11}O_{39})_2WO_2]^{10-}$, or $(A_n)^{10+}[Ru_2(benzene)_2(SiW_{11}O_{39})_2WO_2]^{10-}$ such as $K_{10}[Ru_2(benzene)_2(SiW_{11}O_{39})_2WO_2]$, or $(A_n)^{10+}[Ru_2(P\text{-cymene})_2(SiW_{11}O_{39})_2WO_2]^{10-}$ such as $K_{10}[Ru_2(p\text{-cymene})_2(SiW_{11}O_{39})_2WO_2]$, or $(A_n)^{m+}[Ru_2L_2(GeW_{11}O_{39})_2WO_2]^{m-}$ e.g.

$(A_n)^{10+}[Ru_2(H_2O)_2(GeW_{11}O_{39})_2WO_2]^{10-}$, or $(A_n)^{10+}[Ru_2(benzene)_2(GeW_{11}O_{39})_2WO_2]^{10-}$ such as $K_{10}[Ru_2(benzene)_2(GeW_{11}O_{39})_2WO_2]$, or $(A_n)^{10+}[Ru_2(p\text{-cymene})_2(GeW_{11}O_{39})_2WO_2]^{10-}$ such as $K_{10}[Ru_2p\text{-cymene})_2(GeW_{11}O_{39})_2WO_2]$, or $(A_n)^{m+}[Ru_2L_2(BW_{11}O_{39})_2WO_2]^{m-}$ e.g.

$(A_n)^{12+}[Ru_2(H_2O)_2(BW_{11}O_{39})_2WO_2]^{12-}$, or $(A_n)^{12+}[Ru_2(benzene)_2(BW_{11}O_{39})_2WO_2]^{12-}$ such as $K_{12}[Ru_2(benzene)_2(BW_{11}O_{39})_2WO_2]$, or $(A_n)^{12+}[Ru_2p\text{-cymene})_2(BW_{11}O_{39})_2WO_2]^{12-}$ such as $K_{12}[Ru_2(p\text{-cymene})_2(BW_{11}O_{39})_2WO_2]$, where A, L, m and n, are as described above.

Preferably, the above examples of the POMs according to the invention comprise the α-isomer of the {$XW_{11}O_{39}$} fragment, e.g. $(A_n)^{m+}[Ru_2L_2(\alpha\text{-SiW}_{11}O_{39})_2WO_2]^{m-}$, where A, L and n, are as described above.

The invention also includes solvates of the present POMs. A solvate is an association of solvent molecules with a POM. Preferably, water is associated with the POMs and thus, the POMs according to the invention can in particular be represented by the formulae:

$(A_n)^{m+}[Ru_2L_2(XW_{11}O_{39})_2WO_2]^{m-} \cdot zH_2O$, such as $(A_n)^{m+}[Ru_2L_2(SiW_{11}O_{39})_2WO_2]^{m-} \cdot zH_2O$, $(A_n)^{m+}[Ru_2L_2(GeW_{11}O_{39})_2WO_2]^{m-} \cdot zH_2O$, or $(A_n)^{m+}[Ru_2L_2(BW_{11}O_{39})_2WO_2]^{m-} \cdot zH_2O$, wherein A, n, m, X and L are as described above and wherein z is the number of attracted water molecules per POM molecule and mostly depends on the type of cations A. In some embodiments z is an integer from 1 to 100 such as 10, 21, 23 or 28. In other embodiments, z is an integer from 1 to 50, alternately from 10 to 30.

Suitable examples of the POM solvates according to the invention are represented by the formulae:

$(A_n)^{10+}[Ru_2(H_2O)_2(SiW_{11}O_{39})_2WO_2]^{10-} \cdot zH_2O$, or $(A_n)^{10+}[Ru_2(benzene)_2(SiW_{11}O_{39})_2WO_2]^{10-} \cdot zH_2O$ such as $K_{10}[Ru_2(benzene)_2(SiW_{11}O_{39})_2WO_2] \cdot 10H_2O$, or $(A_n)^{10+}[Ru_2(p\text{-cymene})_2(SiW_{11}O_{39})_2WO_2]^{10-} \cdot zH_2O$ such as $K_{10}[Ru_2(p\text{-cymene})_2(SiW_{11}O_{39})_2WO_2] \cdot 23H_2O$, $(A_n)^{10+}[Ru_2(H_2O)_2(GeW_{11}O_{39})_2WO_2]^{10-} \cdot zH_2O$, $(A_n)^{10+}[Ru_2(benzene)_2(GeW_{11}O_{39})_2WO_2]^{10-} \cdot zH_2O$ such as $K_{10}[Ru_2(benzene)_2(GeW_{11}O_{39})_2WO_2] \cdot 10\ H_2O$, or $(A_n)^{10+}[Ru_2(p\text{-cymene})_2(GeW_{11}O_{39})_2WO_2]^{10-} \cdot zH_2O$ such as $K_{10}[Ru_2(p\text{-cymene})_2(GeW_{11}O_{39})_2WO_2] \cdot 28H_2O$, or $(A_n)^{12+}[Ru_2(H_2O)_2(BW_{11}O_{39})2WO_2]^{12-} \cdot zH_2O$, $(A_n)^{12+}[Ru_2(benzene)_2(BW_{11}O_{39})_2WO_2]^{12-} \cdot zH_2O$ such as $K_{10}[Ru_2(benzene)_2(HBW_{11}O_{39})_2WO_2] \cdot 32H_2O$, or $(A_n)^{12+}[Ru_2(p\text{-cymene})_2(BW_{11}O_{39})_2WO_2]^{12-} \cdot zH_2O$ such as $K_{12}[Ru_2(p\text{-cymene})_2(BW_{11}O_{39})_2WO_2] \cdot 21H_2O$.

where A, n, m, X, z and L are as described above.

The invention is further directed to a process for preparing polyoxometalates according to the invention comprising
(a) reacting a source of Ru and L with $[XW_{11}O_{39}]^{p-}$ to form a salt of $[Ru_2L_2(XW_{11}O_{39})_2WO_2]^{m-}$, (b) optionally adding a salt of A to the salt of $[Ru_2L_2(XW_{11}O_{39})_2WO_2]^{m-}$ to form $(A_n)^{m+}[Ru_2L_2(XW_{11}O_{39})_2WO_2]^{m-}$ or a solvate thereof, and (c) optionally recovering the polyoxometalate obtained in step (a) or step (b), wherein:

y is the charge of the POM precursor $\{XW_{11}O_{39}\}$ and is preferably 8 (when X=Si or Ge) or 9 (when X=B) and A, n, m, X, and L are the same as defined above.

In step (a) a ruthenium precursor is used which comprises at least one ligand L, which is selected from the group consisting of water, unsubstituted or substituted arenes, unsubstituted or substituted heteroarenes, unsaturated hydrocarbons, ethers, unsubstituted or substituted allyl, unsubstituted or substituted alkanes, nitriles, carboxylates, peroxides, peracids, phosphines, phosphanes, CO, OH$^-$, peroxo, carbonate, NO$_3^-$, NO$_2^-$, NO$^-$, NH$_3$, amines, F$^-$, Cl$^-$, Br$^-$, I$^-$, SCN$^-$, NCS$^-$ and NCO$^-$. If ligand L is water, it is possible to use a Ru-precursor comprising water such as water of hydration, e.g. $RuCl_3 \cdot nH_2O$ or $[Ru(H_2O)_6](C_7H_7SO_3)_3$, or to use a Ru-precursor comprising a ligand different from water and subsequently exchange this ligand with water, e.g. by heating the intermediate POM in the presence of water.

In case the ruthenium precursor comprises two or more ligands L, these ligands are independently selected from the above groups. Preferably, L is selected from the group consisting of water, benzene, p-cymene, toluene, mesitylene, durene, hexamethylbenzene, 1,3-dimethylimidazolidine-2-ylidene, 2,2'-bipyridine, ethylene, propylene, α-butylene, cis-β-butylene, trans-β-butylene, isobutylene, n-pentylene, isopentylene, cyclooctadiene, tetrahydrofuran, diethyl ether, methyl t-butyl ether and allyl alcohol. Most preferably, L is water, benzene or p-cymene. Moreover, it is preferred that the source of Ru and L is represented by the formula $[LRuCl_2]_2$, such as $[(benzene)RuCl_2]_2$, $[(p-cymene)RuCl_2]_2$, $[(toluene)RuCl_2]_2$, $[(hexamethylbenzene)RuCl_2]_2$, $[(mesitylene)RuCl_2]_2$, and $[(durene)RuCl_2]_2$. In addition, the ruthenium precursor can also be $[Ru(1,3-dimethylimidazolidine-2-ylidene)_4Cl_2]$, $[Ru(2,2'-bipyridine)_3]Cl_2$, Bis(ethylcyclopentadienyl)ruthenium(II), Bis(pentamethylcyclopentadienyl)ruthenium(II), Chloro(pentamethylcyclopentadienyl)ruthenium(II) tetramer, $RuCl_3 \cdot nH_2O$ or $[Ru(H_2O)_6](C_7H_7SO_3)_2$.

Preferably, the source of Ru and L is $[(benzene)RuCl_2]_2$ or $[(p-cymene)RuCl_2]_2$.

The source of Ru and L is reacted with a salt of $[XW_{11}O_{39}]^{y-}$ such as $K_8[SiW_{11}O_{39}]\cdot 13H_2O$, $K_8[GeW_{11}O_{39}]\cdot 14H_2O$ or $K_8[BW_{11}O_{39}H]\cdot 13H_2O$.

As mentioned above, the structural configuration of the $\{XW_{11}O_{39}\}$ fragment of the present POMs is preferably the α-isomer, i.e. $\{\alpha\text{-}XW_{11}O_{39}\}$. In order to prepare POMs according to the invention comprising $\{\alpha\text{-}XW_{11}O_{39}\}$, it is particularly preferred to use a salt of $[XW_{11}O_{39}]^{y-}$ having a $\beta_2$-configuration, i.e. $[\beta_2\text{-}XW_{11}O_{39}]^{y-}$ such as $[\beta_2\text{-}GeW_{11}O_{39}]^{y-}$. It has surprisingly been found that the use of a salt of $[\beta_2\text{-}XW_{11}O_{39}]^{y-}$ instead of $[\alpha\text{-}XW_{11}O_{39}]^{y-}$ results in the formation of $(A_n)^{m+}[Ru_2L_2(\alpha\text{-}XW_{11}O_{39})_2WO_2]^{m-}$ in a higher yield and purity.

Accordingly, the process according to the invention preferably comprises the preparation of $(A_n)^{m+}[Ru_2L_2(\alpha\text{-}XW_{11}O_{39})_2WO_2]^{m-}$ or a solvate thereof by (a) reacting a source of Ru and L with $[\beta_2\text{-}XW_{11}O_{39}]^{8-}$ to form a salt of $[Ru_2L_2(\alpha\text{-}XW_{11}O_{39})_2WO_2]^{m-}$, (b) optionally adding a salt of A to the salt of $[Ru_2L_2(\alpha\text{-}XW_{11}O_{39})_2WO_2]^{m-}$ to form $(A_n)^{m+}[Ru_2L_2(\alpha\text{-}XW_{11}O_{39})_2WO_2]^{m-}$ or a solvate thereof, and (c) optionally recovering the polyoxometalate obtained in step (a) or step (b), wherein X is a heteroatom selected from Si, Ge and mixtures thereof and in particular is Ge, and A, n, m and L are the same as defined above.

Moreover, it has been found that the course of the reaction of step (a) can be controlled by various parameters such as pH of the reaction mixture, reaction temperature, concentration of the starting materials and counterions used.

In a preferred embodiment, step (a) is carried out in an aqueous solution. The pH of the aqueous solution typically used in step (a) ranges from 1 to 8, preferably from 3 to 5.5 and more preferably from 3.5 to 4.5. Most preferably, a pH of about 4.0 is used. Generally, the pH can be adjusted by the addition of a suitable acid. It is particularly preferred to use an aqueous solution of hydrochloric acid such as HCl (1M).

Moreover, in step (a) it is preferred that the concentration of the Ru ions originating from the source of Ru and L ranges from 0.001 to 1 mol/L, preferably 0.005 to 0.2 mol/L, more preferably 0.01 to 0.05 mol/L, whereas the concentration of the POM precursor $[XW_{11}O_{39}]^{y-}$ preferably ranges from 0.001 to 1 mol/L, preferably 0.005 to 0.2 mol/L, more preferably 0.01 to 0.05 mol/L. The molar ratio between the Ru ions originating from the source of Ru and L and the POM precursor $[XW_{11}O_{39}]^{y-}$ preferably ranges from 3:1 to 1:3, more preferably 2:1 to 1:2 and most preferably is about 1:1.

Furthermore, it is preferred that the reaction mixture is heated during step (a). Preferably, the reaction of the source of Ru and L and the POM precursor is performed at a temperature of 20 to 100° C., preferably 70 to 90° C. Moreover, the reaction mixture is preferably heated for about 5 min to about 4 hours, more preferably for about 10 min to 2 hours, most preferably for about 30 min. Further, it is preferred that the reaction mixture is stirred during step (a).

If at the end of step (a) undesired solids are present, such solids can be removed from the reaction mixture by e.g. filtration. Accordingly, after step (a) the reaction mixture is optionally filtered. Preferably, the reaction mixture is filtered immediately after the end of step (a), i.e. immediately after the stirring is stopped, and is then optionally cooled. More preferably, the heated reaction mixture is cooled first, preferably to room temperature (about 23° C.), and subsequently filtered.

Furthermore, in step (b) a salt of the cation A can be added to the reaction mixture of step (a) or to its filtrate to form $(A_n)^{m+}[Ru_2L_2(XW_{11}O_{39})_2WO_2]^{m-}$. Preferably, the salt of A is added as a solid or in the form of an aqueous solution. In one embodiment, a salt of potassium such as KCl is added in the form of an aqueous solution such as 1.0 M KCl. The counterions of A can be selected from the group consisting of any stable, non-reducing, water soluble anion, e.g. halides, nitrate, sulfate, acetate. Preferably, the chloride salt is used. However, the addition of extra cations A in step (b) is not necessary if the desired cations are already present during step (a), for example as a component of the acid used for adjusting the pH in step (a) or a component of the source of Ru and L or the salt of $[XW_{11}O_{39}]^{y-}$. Preferably, all desired cations are already present during step (a) so that there is no optional addition of extra cations.

In step (c), the POMs according to the invention formed in step (a) or (b) can be recovered. For example, isolation of the POMs can be effected by common techniques including bulk precipitation or crystallization. In particular, the POMs according to the invention can be separated by filtration to obtain red-brown crystals of the present POMs.

The invention is also directed to the use of POMs described herein for catalyzing homogeneous and heterogeneous oxidation reactions of organic substrates. In particular, the present POMs can be used for oxidizing unsubstituted and substituted hydrocarbons such as branched or unbranched alkanes and alkenes having carbon numbers from C1 to C20, preferably from C1 to C6, cycloalkanes, cycloalkenes, aromatic hydrocarbons or mixtures thereof. Examples of suitable organic substrates are methane, ethane, propane, butane, isobutane, pentane, isopentane, neopentane, hexane, ethylene, propylene, α-butylene, cis-β-butylene, trans-β-butylene, isobutylene, n-pentylene, isopentylene, cyclohexane, adamantane, cyclooctadiene, benzene, toluene, o-xylene, m-xylene, p-xylene, mesitylene, durene, hexamethylbenzene, naphthalene, anthracene, phenantrene and mixtures thereof. Since the external ruthenium ions are not sterically shielded by the polyanion backbone and only bear substitution-labile ligands, the coordination sites of ruthenium are easily accessible to the organic substrate and the oxygen transfer molecule and therefore high catalytic activities are achieved. Further, the remarkable thermal stability of the POMs permits their use under a great variety of reaction conditions.

Prior to their use in oxidation reactions, the present POMs can be supported on a solid support. Suitable supports include materials having a high surface area and a pore size which is sufficient to allow the POMs to be loaded, e.g. aerogels of aluminum oxide and magnesium oxide, titanium oxide, zirconium oxide, silica, mesoporous silica, active carbon, zeolites and mesoporous materials. In another embodiment, the supported POMs are further calcined at a temperature not exceeding the transformation temperature of the POM, i.e. the temperature at which decomposition of the POM starts to take place (usually about 400° C. for the present POMs).

If supported, POM loading levels on the support are typically up to 40 wt. % or even more. Accordingly, POM loading levels on the support of 1 to 40 wt. %, particularly 5 to 30 wt. %, and more particularly 5 to 20 wt. % are in general suitable. POM loading levels can be determined by Inductively Coupled Plasma Mass Spectrometry (ICP-MS) analysis or X-ray photoelectron spectroscopy (XPS). In the event the values from the ICP and XPS differ, the ICP shall control. ICP analysis is performed using a Varian Vista MPX. The samples are prepared using microwave digestion by dissolving 10 mg of the supported POM in a mixture of $HNO_3$ (6 ml), HCl (6 ml), HF (1 ml) and $H_2O_2$ (3 ml). After the first run, 6 ml of boric acid (5%) is added and a second run is performed. The quantification is done by Inductively Coupled Plasma Optical Emission Spectrometry (ICP-OES) using calibration curves made between 0 and 50 ppm from standards with known amounts of the respective elements. All tests are conducted twice using a 20 mg sample in the second test. The final volume for each sample is 100 ml.

If the present POMs are used for catalyzing homogeneous and heterogeneous oxidation reactions of organic substrates, commonly suitable oxygen donors such as molecular oxygen, peroxides (e.g. $H_2O_2$, t-$(C_4H_9)$OOH) or peracids (e.g. $CH_3COOOH$) can be used as oxidizing agent. Preferably, the oxidizing agent is an oxygen containing atmosphere. In particular, the oxygen containing atmosphere is air and is preferably constantly passed through the organic substrate (such as an alkane or alkene) at a pressure of 0.01 to 100 bar, preferably 10 to 70 bar.

Moreover, in some embodiments, the oxidation of the organic substrate is preferably carried out at a temperature of 30 to 600° C., preferably 75 to 250° C., preferably 130 to 180° C. In a particularly useful embodiment the oxidation is carried out at a temperature of 100° C. or more, alternately 110° C. or more, alternately 120° C. or more, alternately 130° C. or more, alternately 140° C. or more, alternately 150° C. or more, alternately 160° C. or more, alternately 170° C. or more, alternately 180° C. or more, alternately 190° C. or more, alternately 200° C. or more, alternately 210° C. or more, alternately 220° C. or more.

Another useful aspect of this invention is that the polyoxometalates (supported or unsupported) described herein can be recycled and used multiple times for the oxidation of organic molecules. For example, the POMs according to the invention can be collected after an oxidation reaction, washed with a polar or non-polar solvent such as acetone then dried under heat (typically 50° C. or more, alternately 100° C. or more, alternately 125° C. or more, alternately 150° C. or more) for 30 minutes to 48 hours, typically for 1 to 24 hours, more typically for 2 to 10 hours, more typically for 3 to 5 hours. The recycled POMs (preferably supported) may be used on fresh organic molecules (such as hexadecane) or on recycled organic molecules from a recycle stream.

Advantageously, the supported POMs may be recycled and used again under the same or different reaction conditions. Typically the supported POMs are recycled at least 1 time, preferably at least 4 times, preferably at least 8 times, preferably at least 12 times, preferably at least 100 times.

Thus, this invention also relates to a process for oxidizing organic substrates (typically an alkane) which process comprises contacting a first organic substrate with one or more POMs described herein, thereafter recovering the POMs, contacting the POMs with a solvent (such as acetone) at a temperature of 50° C. or more to obtain a recycled POM, thereafter contacting the recycled POM with a second organic substrate, which may be the same as or different from the first organic substrate, this process may be repeated many times, preferably at least 4 times, preferably at least 8 times, preferably at least 12 times, preferably at least 100 times.

Due to the definite stoichiometry of POMs, the present POMs can be converted (e.g. by calcination at a temperature exceeding the transformation temperature) to mixed metal oxide catalysts in a highly reproducible manner. Consequently, the POMs according to the invention can also be used as a precursor for mixed metal oxide catalysts such as so-called Mitsubishi-type catalysts which are particularly useful for the oxidation of hydrocarbons such as propane.

This invention further relates to:
1. Polyoxometalate represented by the formula

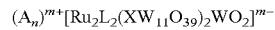

or solvates thereof, wherein
A is a cation,
n is the number of the cations,
m is the charge of the polyanion,
L is a ligand bound to ruthenium and is independently selected from the group consisting of water, unsubstituted or substituted arenes, unsubstituted or substituted heteroarenes, unsaturated hydrocarbons, ethers, unsubstituted or substituted allyl, unsubstituted or substituted alkanes, nitriles, carboxylates, peroxides, peracids, phosphines, phosphanes, CO, OH$^-$, peroxo, carbonate, NO$_3^-$, NO$_2^-$, NO$^{-l,\ NH}{}_3$, amines, F$^-$, Cl$^-$, Br$^-$, I$^-$, SCN$^-$, NCS$^-$, NCO$^-$, and mixtures thereof and
X is a heteroatom selected from Si, Ge, B and mixtures thereof.
2. Polyoxometalate according to paragraph 1, represented by the formula:

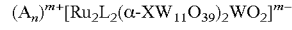

or solvates thereof.
3. Polyoxometalate according to paragraph 1 or 2 or solvates thereof, wherein A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

4. Polyoxymetalate according to any one of paragraphs 1 to 3 or solvates thereof, wherein L is selected from the group consisting of water, unsubstituted or substituted arenes and mixtures thereof.

5. Polyoxymetalate according to any one of paragraphs 1 to 3 or solvates thereof, wherein L is selected from the group consisting of water, benzene, p-cymene, toluene, mesitylene, durene, hexamethylbenzene, 1,3-dimethylimidazolidine-2-ylidene, 2,2'-bipyridine, α- as well as internal olefins with up to 5 carbon atoms such as ethylene, propylene, α-butylene, cis-β-butylene, trans-β-butylene, isobutylene, n-pentylene, and isopentylene, cycloolefins such as cyclooctadiene, tetrahydrofuran, diethyl ether, methyl t-butyl ether, allyl alcohol and mixtures thereof.

6. Polyoxometalate according to any one of paragraphs 1 to 5, represented by the formula:

$$(A_n)^{m+}[Ru_2L_2(XW_{11}O_{39})_2WO_2]^{m-} \cdot zH_2O,$$

wherein z is the number of attracted water molecules per polyoxometalate molecule and ranges from 1 to 100.

7. Process for the preparation of a polyoxometalate according to any one of paragraphs 1 to 6 or a solvate thereof comprising
   (a) reacting a source of Ru and L with $[XW_{11}O_{39}]^{y-}$ to form a salt of $[Ru_2L_2(XW_{11}O_{39})_2WO_2]^{m-}$,
   (b) optionally adding a salt of A to the salt of $[Ru_2L_2(XW_{11}O_{39})_2WO_2]^{m-}$ to form $(A_n)^{m+}[Ru_2L_2(XW_{11}O_{39})_2WO_2]^{m-}$ or a solvate thereof, and
   (c) optionally recovering the polyoxometalate obtained in step (a) or step (b), wherein
   y is the charge of the POM precursor $\{XW_{11}O_{39}\}$ and is 8 for X=Si or Ge, and 9 for X=B and
   A, n, m, L and X are the same as in paragraphs 1 to 6.

8. Process according to paragraph 7, wherein the source of Ru and L is selected from the group consisting of [(benzene)$RuCl_2]_2$, [(p-cymene)$RuCl_2]_2$, [(toluene)$RuCl_2]_2$, [(hexamethylbenzene)$RuCl_2]_2$, [(mesitylene)$RuCl_2]_2$, [(durene)$RuCl_2]_2$,[Ru(1,3-dimethylimidazolidine-2-ylidene)$_4$Cl$_2$], [Ru(2,2'-bipyridine)$_3$]Cl$_2$ and mixtures thereof, and preferably is [(benzene)$RuCl_2]_2$ or [(p-cymene)$RuCl_2]_2$.

9. Process according to paragraph 7 or 8, comprising the preparation of $(A_n)^{m+}[Ru_2L_2(\alpha-XW_{11}O_{39})_2WO_2]^{m-}$ or a solvate thereof by
   (a) reacting a source of Ru and L with $[\beta_2-XW_{11}O_{39}]^{8-}$ to form a salt of $[Ru_2L_2(\alpha-XW_{11}O_{39})_2WO_2]^{m-}$,
   (b) optionally adding a salt of A to the salt of $[Ru_2L_2(\alpha-XW_{11}O_{39})_2WO_2]^{m-}$ to form $(A_n)^{m+}[Ru_2L_2(\alpha-XW_{11}O_{39})_2WO_2]^{m-}$ or a solvate thereof, and
   (c) optionally recovering the polyoxometalate obtained in step (a) or step (b), wherein
   X is a heteroatom selected from Si, Ge and mixtures thereof and in particular is Ge, and
   A, n, m and L are the same as in paragraphs 1 to 6.

10. Process according to any one of paragraphs 7 to 9, wherein step (a) is carried out in an aqueous solution and the pH of the aqueous solution ranges from 1 to 8, preferably from 3 to 5.5.

11. Process according to any one of paragraphs 7 to 10, wherein in step (a) the concentration of the Ru ions originating from the source of Ru and L ranges from 0.001 to 1 mol/L and the concentration of $[XW_{11}O_{39}]^{y-}$ ranges from 0.001 to 1 mol/L.

12. Process according to any one of paragraphs 7 to 11, wherein in step (a) the reaction mixture is heated to a temperature of 20 to 100° C., preferably from 70 to 90° C.

13. Process according to any one of paragraphs 7 to 12, wherein in step (c) the product is isolated by bulk precipitation or crystallization.

14. Use of a polyoxometalate according to any one of paragraphs 1 to 6 or prepared according to any one of claims 7 to 13 or a solvate thereof as catalyst for the homogeneous or heterogeneous oxidation of organic substrates.

15. Use according to paragraph 14, wherein the organic substrates are unsubstituted or substituted hydrocarbons such as branched or unbranched alkanes and alkenes having carbon numbers from C1 to C20, cycloalkanes, cycloalkenes, aromatic hydrocarbons or mixtures thereof.

16. Use according to paragraph 14 or 15, wherein the polyoxometalate is supported on a solid support.

17. Use according to paragraph 16, wherein the supported polyoxometalate is calcined at a temperature not exceeding the transformation temperature of the polyoxometalate.

18. Process for oxidizing organic substrates comprising
   (i) contacting a first organic substrate with one or more polyoxometalates according to any one of claims 1 to 6 or prepared according to any one of claims 7 to 13 or solvates thereof,
   (ii) recovering the polyoxometalates or solvates thereof,
   (iii) contacting the polyoxometalates or solvates thereof with a solvent at a temperature of 50° C. or more to obtain a recycled polyoxometalate or solvate thereof,
   (iv) contacting the recycled polyoxometalate or solvate thereof with a second organic substrate, which may be the same as or different from the first organic substrate, and
   (v) optionally repeating steps (ii) to (iv).

19. Use of a polyoxometalate according to any one of paragraphs 1 to 6 or prepared according to any one of paragraphs 7 to 13 or a solvate thereof as a precursor for preparing mixed metal oxide catalysts.

20. Use according to paragraph 19, wherein the mixed metal oxide catalysts are Mitsubishi-type catalysts.

EXAMPLES

The invention is further illustrated by the following examples.

Example 1

Synthesis of $K_{10}[Ru_2(benzene)_2(\alpha-GeW_{11}O_{39})_2WO_2] \cdot 10H_2O$ using $[\beta_2-GeW_{11}O_{39}]^{8-}$ The samples of $[(C_6H_6)_2RuCl_2]_2$ (0.09 g; 0.18 mmol) and $K_8[\beta_2-GeW_{11}O_{39}] \cdot 14H_2O$ (1.18 g; 0.36 mmol) (synthesized according to Nsouli et al., *Inorg. Chem.*, 2006, 45, 3858) were dissolved with stirring and heating to 80° C. for 10 min in 15 mL of water. By adding a few drops of 1M HCl the pH was adjusted to 3.9. The reaction mixture was heated to 80° C. for 20 min, with the final pH being 5.0. A small amount of an orange precipitate was filtered off. Then, 2 mL of 1.0 M KCl solution was added to the solution. Slow evaporation at room temperature led to a dark brown crystalline product in one week which was recrystallized from hot water (yield 0.70 g, 60%).

IR (cm$^{-1}$): 952(s), 882(s), 820(s), 792(sh), 757(sh), 690(s), 619(sh), 527(m), 468(m) (measured on a Nicolet-Avatar 370 spectrometer using KBr pellets).

Besides IR, the product was also characterized by single-crystal XRD. The crystal data and structure refinement obtained on a Bruker Kappa APEX II instrument using the SHELXTL software package are shown in the following Table.

TABLE 1

Crystal data and structure refinement for
$K_{10}[Ru_2(benzene)_2(\alpha\text{-}GeW_{11}O_{39})_2WO_2]\cdot 10H_2O$

| | |
|---|---|
| Empirical formula | C12 H32 Ge2 K10 O90 Ru2 W23 |
| Formula weight | 6583.2 |
| Temperature | 296(2) K |
| Wavelength | 0.71073 Å |
| Crystal system | Monoclinic |
| Space group | P2(1)/c |
| Unit cell dimensions | a = 23.1277(10) Å   α = 90° |
| | b = 19.6387(8) Å   β = 117.762(1)° |
| | c = 24.4712(9) Å   γ = 90° |
| Volume | 9835.3(7) Å$^3$ |
| Z | 4 |
| Density (calculated) | 4.445 Mg/m$^3$ |
| Absorption coefficient | 28.201 mm$^{-1}$ |
| F(000) | 11464 |
| Crystal size | 0.16 × 0.13 × 0.05 mm$^3$ |
| Theta range for data collection | 3.79 to 22.21° |
| Index ranges | −24 <= h <= 24, −20 <= k <= 20, −25 <= l <= 26 |
| Reflections collected | 170551 |
| Independent reflections | 12308 [R(int) = 0.2109] |
| Completeness to theta = 22.21° | 99.2% |
| Absorption correction | Semi-empirical from equivalents |
| Max. and min. transmission | 0.3273 and 0.0995 |
| Refinement method | Full-matrix least-squares on F$^2$ |
| Data/restraints/parameters | 12308/0/717 |
| Goodness-of-fit on F$^2$ | 1.061 |
| Final R indices [I > 2sigma(I)] | R1 = 0.0567, wR2 = 0.1202 |
| R indices (all data) | R1 = 0.1250, wR2 = 0.1571 |
| Largest diff. peak and hole | 3.080 and −2.824 e.Å$^{-3}$ |

Mg/m$^3$ = Mega gram per cubic meter

Example 2

Synthesis of $K_{10}[Ru_2(p\text{-}cymene)_2(\alpha\text{-}GeW_{11}O_{39})_2 WO_2]\cdot 28H_2O$ using $[\beta_2\text{-}GeW_{11}O_{39}]^{8-}$

[(p-cymene)$_2$RuCl$_2$]$_2$ (0.110 g; 0.18 mmol) and K$_8$[β$_2$-GeW$_{11}$O$_{39}$] 14H$_2$O (1.18 g; 0.36 mmol) (synthesized according to Nsouli et al., Inorg. Chem., 2006, 45, 3858) were dissolved with stirring and heating to 80° C. for 15 min in 15 mL of water. The initial pH was 5.0. By adding few drops of 1M HCl the pH was adjusted to 4.0. The reaction mixture was heated to 80° C. for 15 min, with the final pH being 4.5. A small amount of a dark precipitate was filtered off. Then, 2 mL of 1.0 M KCl solution was added to the orange solution. Slow evaporation at room temperature led to a dark orange crystalline product in the form of plates and needles) in one week (yield 0.582 g, 50%).

IR (cm−1): 952(s), 886(s), 821(s), 791(sh), 758(s), 719 (sh), 687(s), 527(m), 483(sh), 469(m) (measured on a Nicolet-Avatar 370 spectrometer using KBr pellets).

TABLE 2

Crystal data and structure refinement obtained on a Bruker Kappa APEX II instrument using the SHELXTL software package for
$K_{10}[Ru_2(p\text{-}cymene)_2(\alpha\text{-}GeW_{11}O_{39})_2WO_2]\cdot 28H_2O$

| | |
|---|---|
| Empirical formula | C20 H84 Ge2 K10 O108 Ru2 W23 |
| Formula weight | 7019.5 |
| Space group | P2(1)/n |
| a (Å) | 12.9410(3) |
| b (Å) | 19.2466(4) Å |
| c (Å) | 47.3506(14) Å |
| α (°) | 90 |
| β (°) | 92.818(2) |
| γ (°) | 90 |
| vol (Å$^3$) | 11779.4(5) |
| Z | 4 |
| temp (° C.) | −100 |
| wavelength (Å) | 0.71073 |
| d$_{calcd}$ (Mg m$^{-3}$) | 0.99 |
| abs coeff. (mm$^{-1}$) | 11.818 |
| Final R indices [I > 2sigma(I)] | R1 = 0.0923, wR2 = 0.2304 |
| R indices (all data) | R1 = 0.1234, wR2 = 0.2501 |

Example 3

Synthesis of $K_{10}[Ru_2(benzene)_2(\alpha\text{-}GeW_{11}O_{39})_2 WO_2]\cdot 10H_2O$ using $[\alpha\text{-}GeW_{11}O_{39}]^{8-}$

[(C$_6$H$_6$)$_2$RuCl$_2$]$_2$ (0.09 g; 0.18 mmol) and K$_6$Na$_2$[α-GeW$_{11}$O$_{39}$] 13H$_2$O (1.164 g; 0.36 mmol) (synthesized according to Tézé et al., J. Inorg. Nucl. Chem., 1977, 39, 999, followed by purification via recrystallization from hot water) were dissolved with stirring and heating to 80° C. for 10 min in 15 mL of water. The initial pH was 4.7. By adding few drops of 1M HCl the pH was adjusted to 4.0. The reaction mixture was heated to 80° C. for 20 min, with the final pH being 4.3. A small amount of an orange precipitate was filtered off. Then, 2 mL of 1.0 M KCl solution were added to the orange solution. Slow evaporation at room temperature led to an inseparable crystalline mixture of the desired title compound (dark red plates) as well as unwanted side-products (light orange blocks and orange needles) in one week. Recrystallization from hot water still resulted in a mixture of compounds.

Example 4

Synthesis of $K_{10}[Ru_2(p\text{-}cymene)_2(\alpha\text{-}GeW_{11}O_{39})_2 WO_2]\cdot 28H_2O$ using $[\alpha\text{-}GeW_{11}O_{39}]^{8-}$

[(p-cymene)$_2$RuCl$_2$]$_2$ (0.110 g; 0.18 mmol) and K6Na$_2$[α-GeW$_{11}$O$_{39}$] 13H$_2$O (1.164 g; 0.36 mmol) (synthesized according to Tézé et al., J. Inorg. Nucl. Chem., 1977, 39, 999, followed by purification via recrystallization from hot water) were dissolved with stirring and heating to 80° C. for 15 min in 15 mL of water. The initial pH was 5.5. By adding a few drops of 1M HCl the pH was adjusted to 4.0. The reaction mixture was heated to 80° C. for 15 min, the final pH was 4.2. A small amount of a dark precipitate was filtered off. Then, 2 mL of 1.0 M KCl solution was added to the orange solution. Slow evaporation at room temperature led to the desired title compound (dark orange plates) as well as unwanted side-products (light orange needles) in one week. Both products could be separated under the microscope and after recrystallization the yield for the desired product was 0.366 g (31%).

IR (cm−1): 952(s), 886(s), 821(s), 791(sh), 758(s), 719 (sh), 687(s), 527(m), 483(sh), 469(m).

Example 5

Synthesis of $K_{10}[Ru_2(benzene)_2(\alpha\text{-}SiW_{11}O_{39})_2 WO_2]\cdot 10OH_2O$

[$(C_6H_6)_2RuCl_2]_2$ (0.09 g; 0.18 mmol) and $K_8[\alpha\text{-}SiW_{11}O_{39}]\cdot 13H_2O$ (1.16 g; 0.36 mmol) (synthesized according to Tézé et al., *J. Inorg. Nucl. Chem.* 1977, 39, 999) were dissolved with stirring and heating to 85° C. for 10 min in 20 mL of water. By adding few drops of 1M HCl the pH was adjusted to 4.0. The reaction mixture was heated to 85° C. for 20 min, the final pH was 5.5. A small amount of an orange precipitate was filtered off. Then, 2 mL of 1.0 M KCl solution was added. Slow evaporation at room temperature led to a dark brown crystalline product in one week (yield 0.467 g, 41%).

IR (cm−1): 1011(m), 956(s), 908(sh), 888(s), 825(sh), 805 (sh), 772(s), 727(sh), 699(s), 668(sh), 616(m), 547(sh), 523 (m) (measured on a Nicolet-Avatar 370 spectrometer using KBr pellets).

The product was further characterized by single crystal XRD.

TABLE 3

Crystal data and structure refinement obtained on a Bruker Kappa APEX II instrument using the SHELXTL software package for $K_{10}[Ru_2(benzene)_2(\alpha\text{-}SiW_{11}O_{39})_2WO_2]\cdot 10H_2O$

| | |
|---|---|
| Empirical formula | C12 H22 K10 O90 Ru2 Si2 W23 |
| Formula weight | 6484.2 |
| Temperature | 296(2) K |
| Wavelength | 0.71073 Å |
| Crystal system | Triclinic |
| Space group | P-1 |
| Unit cell dimensions | a = 14.4147(8) Å   α = 108.068(3)° |
| | b = 16.2554(11) Å   β = 106.688(3)° |
| | c = 22.7113(15) Å   γ = 96.463(3)° |
| Volume | 4725.9(5) Å³ |
| Z | 2 |
| Density (calculated) | 4.557 Mg/m³ |
| Absorption coefficient | 28.747 mm⁻¹ |
| F(000) | 5644 |
| Crystal size | 0.38 × 0.08 × 0.08 mm³ |
| Theta range for data collection | 2.70 to 27.59° |
| Index ranges | −18 <= h <= 18, −21 <= k <= 21, −28 <= l <= 29 |
| Reflections collected | 277066 |
| Independent reflections | 21494 [R(int) = 0.0990] |
| Completeness to theta = 27.59° | 98.1% |
| Absorption correction | Semi-empirical from equivalents |
| Max. and min. transmission | 0.2042 and 0.0553 |
| Refinement method | Full-matrix least-squares on F² |
| Data/restraints/parameters | 21494/0/754 |
| Goodness-of-fit on F² | 1.018 |
| Final R indices [I > 2sigma(I)] | R1 = 0.0475, wR2 = 0.1156 |
| R indices (all data) | R1 = 0.0937, wR2 = 0.1395 |
| Largest diff. peak and hole | 3.004 and −2.910 e.Å⁻³ |

Mg/m³ = Mega gram per cubic meter

Example 6

Synthesis of $K_{10}[Ru_2(p\text{-}cymene)_2(\alpha\text{-}SiW_{11}O_{39})_2 WO_2]\cdot 23H_2O$ A sample of 0.110 g (0.18 mmol) of [Ru(p-cymene)Cl$_2$]$_2$ was dissolved in 20 mL H$_2$O and then 1.159 g (0.36 mmol) of $K_8[\alpha\text{-}SiW_{11}O_{39}]\cdot 13H_2O$ (synthesized according to Tézé et al., *Inorg. Synth.* 1990, 89) were added. The pH of the solution was adjusted to 4.0 by the addition of HCl (1M). Then, the solution was heated to 80° C. for 30 minutes, cooled to room temperature, and filtered. Then, 1 mL of 1M KCl solution was added. Colorless crystals of paratungstates were filtered after 3 days. Slow evaporation of the filtrate at room temperature led to dark orange crystals of the product after ten days (yield 0.336 g, 34%).

IR (cm−1): 1011 (w), 955 (m), 891 (s), 824 (s), 804 (s), 770 (m), 696 (s), 524 (m) cm⁻¹. (measured on a Nicolet-Avatar 370 spectrometer using KBr pellets).

The product was further characterized by single crystal XRD.

TABLE 4

Crystal data and structure refinement obtained on a Bruker Kappa APEX II instrument using the SHELXTL software package for $K_{10}[Ru_2(p\text{-}cymene)_2(\alpha\text{-}SiW_{11}O_{39})_2WO_2]\cdot 23H_2O$

| | |
|---|---|
| Empirical formula | C20 H82 K12 O127 Ru2 Si2.5 W29 |
| Formula weight | 8427.7 |
| Space group | P-1 |
| a (Å) | 12.5854(2) |
| b (Å) | 19.5288(4) |
| c (Å) | 30.8424(7) |
| α (°) | 106.8880(10) |
| β (°) | 91.6830(10) |
| γ (°) | 104.3440(10) |
| vol (Å³) | 6985.2(2) |
| Z | 1 |
| Temp (° C.) | −100 |
| wavelength (Å) | 0.71073 |
| d$_{calcd}$ (Mg m⁻³) | 2.00 |
| abs coeff. (mm⁻¹) | 24.341 |
| Final R indices [I > 2sigma(I)] | R1 = 0.0612, wR2 = 0.1539 |
| R indices (all data) | R1 = 0.1215, wR2 = 0.1885 |

Example 7

Synthesis of $K_{10}[Ru_2(benzene)_2(\alpha\text{-}HBW_{11}O_{39})_2 WO_2]\cdot 32H_2O$

[$(C_6H_6)_2RuCl_2]_2$ (0.09 g; 0.18 mmol) and $K_8[\alpha\text{-}BW_{11}O_{39}H]\cdot 13H_2O$ (1.16 g; 0.36 mmol) (synthesized according to Tézé et al., *Inorg. Chem.* 1997, 36, 505; the precursor contained paratungstate impurities) were dissolved with stirring and heating to 80° C. for 10 min in 20 mL of water. By adding few drops of 1M HCl the pH was adjusted to 4.0. The reaction mixture was heated to 80° C. for 20 min, the final pH was 5.1. A small amount of an orange precipitate was filtered off. Then, 2 mL of 1.0 M KCl solution was added to the filtrate. Slow evaporation at room temperature led to light orange crystalline paratungstate product in one week, which was filtered off. Further evaporation at room temperature led to a dark red crystalline product (yield 0.250 g, 21%).

IR (cm−1): 999(m), 949(s), 888(sh), 855(sh), 831(s), 768(s), 712(s), 618(m) 520(m) (measured on a Nicolet-Avatar 370 spectrometer using KBr pellets).

The product was further characterized by single crystal XRD.

TABLE 5

Crystal data and structure refinement obtained on a Bruker Kappa APEX II instrument using the SHELXTL software package for $K_{10}[Ru_2(benzene)_2(\alpha\text{-}HBW_{11}O_{39})_2WO_2]\cdot 32H_2O$

| | |
|---|---|
| Empirical formula | C12 H78 B2 K10 O112 Ru2 W23 |
| Formula weight | 6858.1 |
| Temperature | 173(2) K |

TABLE 5-continued

Crystal data and structure refinement obtained on a Bruker Kappa APEX II instrument using the SHELXTL software package for $K_{10}[Ru_2(benzene)_2(\alpha-HBW_{11}O_{39})_2WO_2] \cdot 32H_2O$

| | |
|---|---|
| Wavelength | 0.71073 Å |
| Crystal system | Triclinic |
| Space group | P-1 |
| Unit cell dimensions | a = 12.426(3) Å   a = 87.579(16)° |
| | b = 19.575(5) Å   b = 87.220(14)° |
| | c = 23.144(7) Å   g = 75.203(13)° |
| Volume | 5434(3) Å³ |
| Z | 2 |
| Density (calculated) | 4.192 Mg/m³ |
| Absorption coefficient | 25.008 mm⁻¹ |
| F(000) | 6072 |
| Crystal size | 0.37 × 0.22 × 0.16 mm³ |
| Theta range for data collection | 2.35 to 27.70° |
| Index ranges | −16 <= h <= 16, −25 <= k <= 25, |
| | −30 <= l <= 30 |
| Reflections collected | 237879 |
| Independent reflections | 25048 [R(int) = 0.1060] |
| Completeness to theta = 27.70° | 98.3% |
| Absorption correction | Semi-empirical from equivalents |
| Max. and min. transmission | 0.1059 and 0.0227 |
| Refinement method | Full-matrix least-squares on F² |
| Data/restraints/parameters | 25048/0/820 |
| Goodness-of-fit on F² | 1.018 |
| Final R indices [I > 2sigma(I)] | R1 = 0.0531, wR2 = 0.1344 |
| R indices (all data) | R1 = 0.0805, wR2 = 0.1511 |
| Largest diff. peak and hole | 3.992 and −3.855 e.A⁻³ |

Mg/m³ = Mega gram per cubic meter

Example 8

Synthesis of $K_{12}[Ru_2(p\text{-cymene})]_2(\alpha\text{-BW}_{11}O_{39})_2 WO_2] \cdot 21H_2O$ A sample of 0.121 g (0.20 mmol) of [Ru(p-cymene)Cl₂]₂ was dissolved in 10 mL of H₂O and then 1.154 g (0.36 mmol) of K₈[α-BW₁₁O₃₉H].13H₂O (synthesized according to Tézé et al., *Inorg. Chem.* 1997, 36, 505) was added. The pH of the solution was adjusted to 4.0 by the addition of HCl (1M). Then, the solution was heated to 80° C. for 30 minutes, cooled to room temperature, and filtered. Then, 8 mL of 1M KCl solution were added. Colorless crystals of paratungstates were filtered off after 36 hours. Slow evaporation of the filtrate at room temperature led to the formation of pure dark orange crystals within one week (yield 0.190 g, 14%).

IR (cm−1): 999 (w), 950 (s), 908 (sh), 892 (s), 850 (s), 826 (s), 768 (m), 711 (s), 519 (w) cm⁻¹. (measured on a Nicolet-Avatar 370 spectrometer using KBr pellets).

Besides IR, the product was also characterized by single-crystal XRD. The crystal data and structure refinement obtained on a Bruker Kappa APEX II instrument using the SHELXTL software package are shown in the following Table.

TABLE 6

Crystal data and structure refinement for $K_{12}[Ru_2(p\text{-cymene})_2(\alpha\text{-BW}_{11}O_{39})_2WO_2] \cdot 21H_2O$

| | |
|---|---|
| Empirical formula | C20 H70 B2 K12 O101 Ru2 W23 |
| Formula weight | 6848.0 |
| Space group | P2(1)/c |
| a (Å) | 12.9020(7) |
| b (Å) | 19.0614(10) |
| c (Å) | 43.785(3) |
| α (°) | 90 |
| β (°) | 92.522(3) |

TABLE 6-continued

Crystal data and structure refinement for $K_{12}[Ru_2(p\text{-cymene})_2(\alpha\text{-BW}_{11}O_{39})_2WO_2] \cdot 21H_2O$

| | |
|---|---|
| γ (°) | 90 |
| vol (Å³) | 10757.6(10) |
| Z | 4 |
| Temp (° C.) | −100 |
| wavelength (Å) | 0.71073 |
| d$_{calcd}$ (Mg m⁻³) | 1.06 |
| abs coeff. (mm⁻¹) | 24.994 |
| Final R indices [I > 2sigma(I)] | R1 = 0.0704, wR2 = 0.1874 |
| R indices (all data) | R1 = 0.1087, wR2 = 0.2249 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A polyoxometalate represented by the formula:

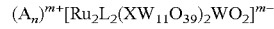

or solvates thereof, wherein
A is a cation,
n is the number of the cations,
m is the charge of the polyanion,
L is a ligand bound to ruthenium and is independently selected from the group consisting of water, unsubstituted or substituted arenes, unsubstituted or substituted heteroarenes, unsaturated hydrocarbons, ethers, unsubstituted or substituted allyl, unsubstituted or substituted alkanes, nitriles, carboxylates, peroxides, peracids, phosphines, phosphanes, CO, OH⁻, peroxo, carbonate, NO₃⁻, NO₂⁻, NO⁻, NH₃, amines, F⁻, Cl⁻, Br⁻, I⁻, SCN⁻, NCS⁻, NCO⁻, and mixtures thereof and
X is a heteroatom selected from Si, Ge, B and mixtures thereof.

2. The polyoxometalate of claim 1, wherein the (XW₁₁O₃₉) fragments are in the form of the α-isomer.

3. The polyoxometalate according to claim 1 or solvates thereof, wherein A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

4. The polyoxymetalate of claim 1 or solvates thereof, wherein L is selected from the group consisting of water, unsubstituted or substituted arenes and mixtures thereof.

5. The polyoxymetalate of claim 1 or solvates thereof, wherein L is selected from the group consisting of water, benzene, p-cymene, toluene, mesitylene, durene, hexamethylbenzene, 1,3-dimethylimidazolidine-2-ylidene, 2,2'-bipyridine, α- as well as internal olefins with up to 5 carbon atoms such as ethylene, propylene, α-butylene, cis-β-butylene, trans-β-butylene, isobutylene, n-pentylene, and isopentylene, cycloolefins such as cyclooctadiene, tetrahydrofuran, diethyl ether, methyl t-butyl ether, allyl alcohol and mixtures thereof.

6. A solvate of the polyoxymetalate of claim 1, represented by the formula:

$(A_n)^{m+}[Ru_2L_2(XW_{11}O_{39})_2WO_2]^{m-}\cdot zH_2O,$ wherein z is the number of attracted water molecules per polyoxometalate molecule and ranges from 1 to 100, and A, n, m, L, and X are as defined in claim 1.

7. A process for the preparation of a polyoxometalate, or a solvate thereof, represented by the formula:

$(A_n)^{m-}[Ru_2L_2(XW_{11}O_{39})_2WO_2]^{m-}\cdot zH_2O,$ or $(A_n)^{m+}[Ru_2L_2(XW_{11}O_{39})_2WO_2]^{m-}$ wherein
A is a cation,
n is the number of the cations,
m is the charge of the polyanion,
L is a ligand bound to ruthenium and is independently selected from the group consisting of water, unsubstituted or substituted arenes, unsubstituted or substituted heteroarenes, unsaturated hydrocarbons, ethers, unsubstituted or substituted allyl, unsubstituted or substituted alkanes, nitriles, carboxylates, peroxides, peracids, phosphines, phosphanes, CO, OH⁻, peroxo, carbonate, $NO_3^-$, $NO_2^-$, $NO^-$, $NH_3$, amines, F⁻, Cl⁻, Br⁻, I⁻, SCN⁻, NCS⁻, NCO⁻, and mixtures thereof,
X is a heteroatom selected from Si, Ge, B and mixtures thereof, and
z is the number of attracted water molecules per polyoxometalate molecule and ranges from 1 to 100;
said process comprising:
(a) reacting a source of Ru and L with $[XW_{11}O_{39}]^{y-}$ to form a salt of $[Ru_2L_2(XW_{11}O_{39})_2WO_2]^{m-}$,
(b) optionally adding a salt of A to the salt of $[Ru_2L_2(XW_{11}O_{39})_2WO_2]^{m-}$ to form $(A_n)^{m+}[Ru_2L_2(XW_{11}O_{39})_2WO_2]^{m-}$ or a solvate thereof, and
(c) optionally recovering the polyoxometalate obtained in step (a) or step (b),
wherein
y is the charge of the POM precursor $\{XW_{11}O_{39}\}$ and is 8 when X=Si or Ge, and 9 when X=B.

8. The process of claim 7, wherein the source of Ru and L is selected from the group consisting of [(benzene)RuCl₂]₂, [(p-cymene)RuCl₂]₂, [(toluene)RuCl₂]₂, [(hexame-thylbenzene)RuCl₂]₂, [(mesitylene)RuCl₂]₂, [(durene)RuCl₂]₂, [Ru(1,3-dimethylimidazolidine-2-ylidene)₄Cl₂], [Ru(2,2'-bipyridine)₃]Cl₂ and mixtures thereof, and preferably is [(benzene)RuCl₂]₂ or [(p-cymene)RuCl₂]₂.

9. The process of claim 7, comprising the preparation of $(A_n)^{m+}[Ru_2L_2(\alpha-XW_{11}O_{39})_2WO_2]^{m-}$ or a solvate thereof by
(a) reacting a source of Ru and L with $[\beta_2-XW_{11}O_{39}]^{8-}$ to form a salt of $[Ru_2L_2(\alpha-XW_{11}O_{39})_2WO_2]^{m-}$,
(b) optionally adding a salt of A to the salt of $[Ru_2L_2(\alpha-XW_{11}O_{39})_2WO_2]^{m-}$ to form $(A_n)^{m+}[Ru_2L_2(\alpha-XW_{11}O_{39})_2WO_2]^{m-}$ or a solvate thereof, and
(c) optionally recovering the polyoxometalate obtained in step (a) or step (b), wherein
X is a heteroatom selected from Si, Ge and mixtures thereof, and A, n, m and L are as defined in claim 7.

10. The process of claim 7, wherein step (a) is carried out in an aqueous solution and the pH of the aqueous solution ranges from 1 to 8.

11. The process of claim 7, wherein in step (a) the concentration of the Ru ions originating from the source of Ru and L ranges from 0.001 to 1 mol/L and the concentration of $[XW_{11}O_{39}]^{y-}$ ranges from 0.001 to 1 mol/L.

12. The process of claim 7, wherein in step (a) the reaction mixture is heated to a temperature of 20 to 100° C.

13. The process of claim 7, wherein in step (c) the product is isolated by bulk precipitation or crystallization.

14. A process for the homogeneous or heterogeneous oxidation of organic substrates comprising contacting the polyoxometalate of claim 1 with an organic substrate.

15. The process of claim 14, wherein the organic substrate is selected from the group consisting of branched or unbranched alkanes having carbon numbers from C1 to C20, branched or unbranched alkenes having carbon numbers from C1 to C20, cycloalkanes, cycloalkenes, aromatic hydrocarbons or mixtures thereof.

16. The process of claim 14, wherein the polyoxometalate is supported on a solid support.

17. The process of claim 16, wherein the supported polyoxometalate is calcined at a temperature not exceeding the transformation temperature of the polyoxometalate.

18. A Process for oxidizing organic substrates comprising
(i) contacting a first organic substrate with one or more polyoxometalates of claim 1,
(ii) recovering the polyoxometalates or solvates thereof,
(iii) contacting the polyoxometalates or solvates thereof with a solvent at a temperature of 50° C. or more to obtain a recycled polyoxometalate or solvate thereof,
(iv) contacting the recycled polyoxometalate or solvate thereof with a second organic substrate, which may be the same as or different from the first organic substrate, and
(v) optionally repeating steps (ii) to (iv).

19. A process to prepare a mixed metal oxide catalyst comprising calcining the polyoxometalates of claim 1 at a temperature exceeding the transformation temperature of the polyoxometalates.

20. The process of claim 19, wherein the mixed metal oxide catalysts are Mitsubishi-type catalysts.

21. The process of claim 18 wherein the polyoxometalate is recycled at least 4 times.

22. The process of claim 14 wherein an oxygen donor is present during the oxidation.

23. The process of claim 14 wherein air is constantly passed through the organic substrate during the oxidation.

24. The process of claim 14 wherein the oxidation takes place at a temperature of 30 to 600° C.

25. The process of claim 14 wherein an oxygen donor is present during the oxidation and the oxygen donor is air.

* * * * *